United States Patent
Murray

(10) Patent No.: US 6,974,483 B2
(45) Date of Patent: Dec. 13, 2005

(54) MODULAR NECK FOR FEMUR REPLACEMENT SURGERY

(75) Inventor: Ian P. Murray, Phoenix, MD (US)

(73) Assignee: Encore Medical Corporation, Hunt Valley, MD (US)

(*) Notice: Subject to any disclaimer, the term of this patent is extended or adjusted under 35 U.S.C. 154(b) by 140 days.

(21) Appl. No.: 10/272,208

(22) Filed: Oct. 15, 2002

(65) Prior Publication Data

US 2003/0074080 A1 Apr. 17, 2003

Related U.S. Application Data

(63) Continuation-in-part of application No. 09/505,876, filed on Feb. 17, 2000, now Pat. No. 6,464,728, which is a continuation-in-part of application No. 09/059,698, filed on Apr. 14, 1998, now abandoned.

(51) Int. Cl.[7] .............................. A61F 2/36; A61F 2/30
(52) U.S. Cl. ............................. 623/22.42; 623/22.46; 623/23.47
(58) Field of Search ................ 623/20.15, 22.41–22.46, 623/23.18, 23.22, 23.23, 23.35, 23.45–23.48, 623/23.52

(56) References Cited

U.S. PATENT DOCUMENTS

| | | |
|---|---|---|
| 3,067,740 A | 12/1962 | Haboush |
| 3,874,003 A | 4/1975 | Moser et al. |
| 4,608,055 A | 8/1986 | Morrey et al. |
| 4,878,917 A | 11/1989 | Kranz et al. |
| 4,888,023 A | 12/1989 | Averill et al. |
| 4,892,546 A | 1/1990 | Kotz et al. |
| 4,908,032 A | 3/1990 | Keller |
| 4,919,670 A | 4/1990 | Dale et al. |
| 4,950,300 A | 8/1990 | Laglais |
| 4,995,883 A | 2/1991 | Demane et al. |
| 5,002,578 A | 3/1991 | Luman |
| 5,002,581 A | 3/1991 | Paxson et al. |
| 5,030,234 A | 7/1991 | Pappas et al. |
| 5,057,101 A | 10/1991 | Dorr et al. |
| 5,108,452 A | 4/1992 | DeMane et al. |
| 5,286,260 A | 2/1994 | Bolesky et al. |
| 5,314,479 A | 5/1994 | Rockwood, Jr. et al. |
| 5,358,526 A | 10/1994 | Tormer |
| 5,480,451 A | 1/1996 | Grundei et al. |
| 5,489,309 A | 2/1996 | Lackey et al. |
| 5,653,764 A | 8/1997 | Murphy |
| 5,653,765 A | 8/1997 | McTighe et al. |

FOREIGN PATENT DOCUMENTS

| | | | |
|---|---|---|---|
| EP | 0 187 903 A1 * | 7/1986 | .............. A61F 2/36 |
| EP | 0 201 407 A1 | 11/1986 | |
| EP | 0 457 222 A1 | 11/1991 | |
| FR | 2 616 060 A1 | 12/1988 | |
| FR | 2 640 497 A | 6/1990 | |

(Continued)

Primary Examiner—David H. Willse
(74) Attorney, Agent, or Firm—Armstrong, Kratz, Quintos, Hanson & Brooks, LLP

(57) ABSTRACT

A prosthesis device for hip surgery replacement has a main body portion which is implanted in the femur of a patient. A series of adapters are provided from which one is selected. Each adapter has a tapered shank which is received a corresponding tapered bore in the main body portion forming a first lock therein. The adapter has tapered teeth which engage corresponding tapered teeth in the bore in the main body portion, forming a second lock. The adapter is indexed with respect to the main body portion. A method of use is disclosed.

12 Claims, 11 Drawing Sheets

FOREIGN PATENT DOCUMENTS

| | | | | | | |
|---|---|---|---|---|---|---|
| FR | 2 677 879 A1 | 12/1992 | | | | |
| FR | 2 689 001 A1 | 10/1993 | | | | |
| FR | 2 693 367 A1 | 1/1994 | | | | |
| FR | 2 697 966 | 5/1994 | | | | |
| FR | 2 763 501 A1 * | 11/1998 | ............. A61F 2/40 | | | |
| FR | 2 788 429 A1 * | 7/2000 | ............. A61F 2/36 | | | |
| FR | 2 788 429 A1 | 7/2002 | | | | |
| WO | 91/03992 | 4/1991 | | | | |
| WO | 94/07438 A | 4/1994 | | | | |
| WO | WO 00/64384 * | 11/2000 | ............. A61F 2/36 | | | |

\* cited by examiner

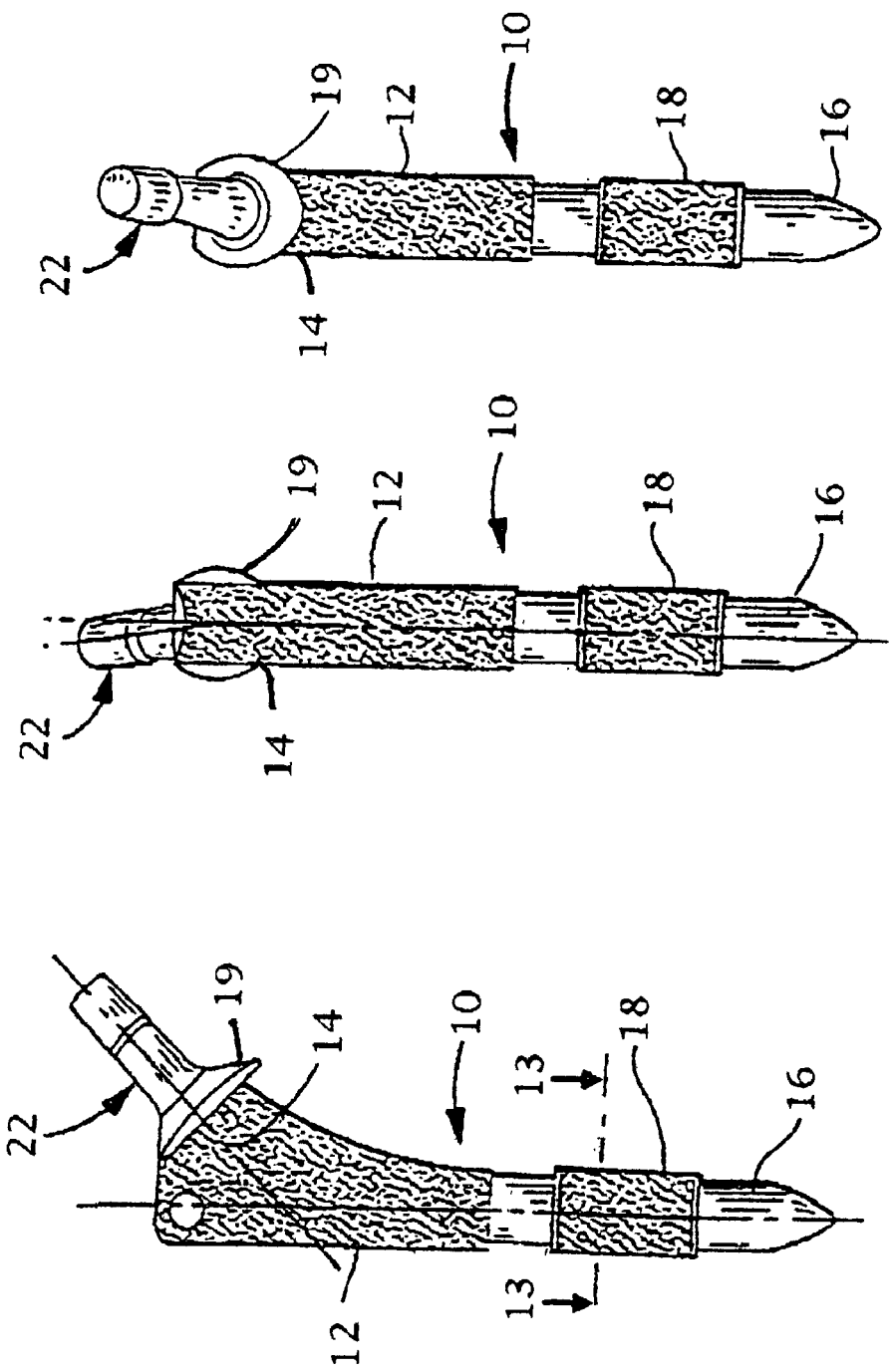

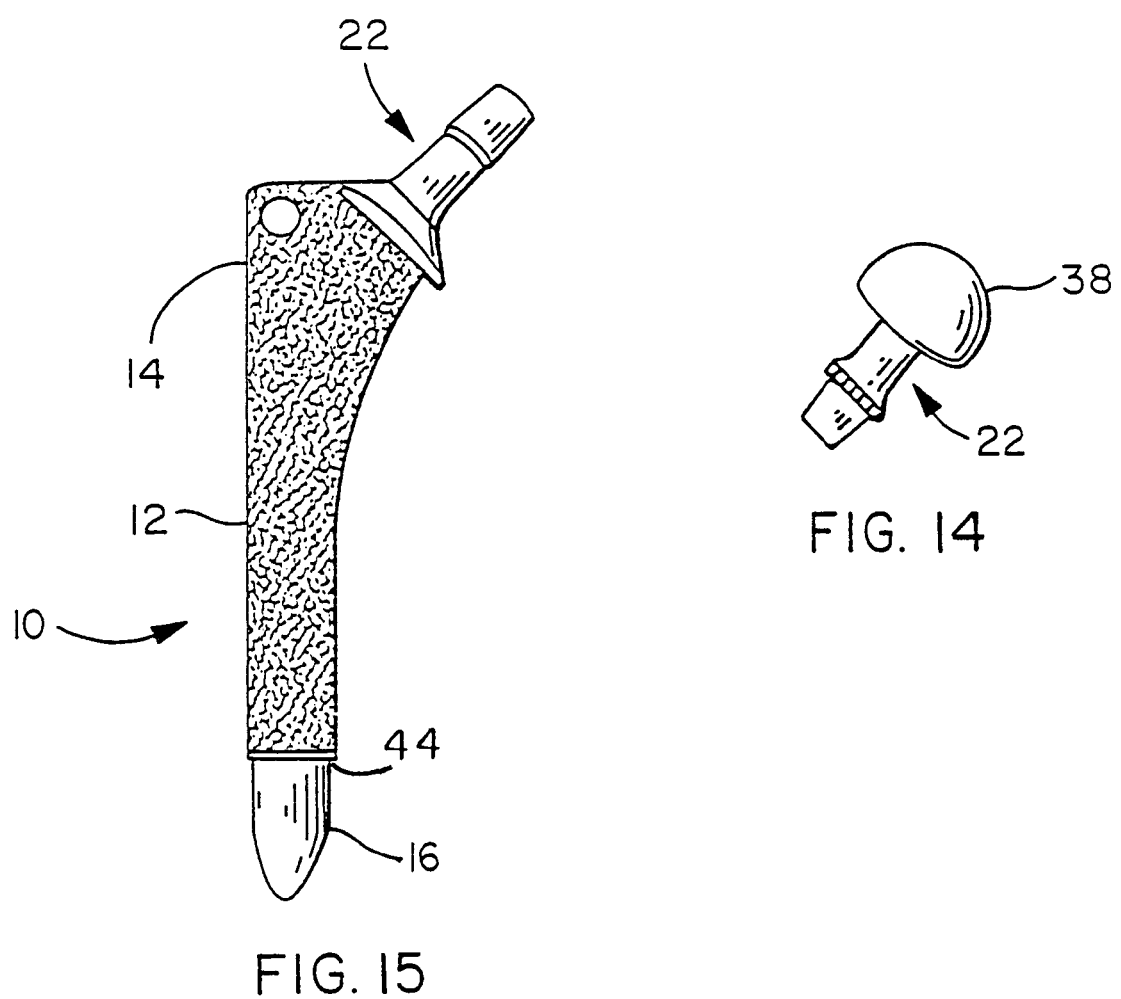

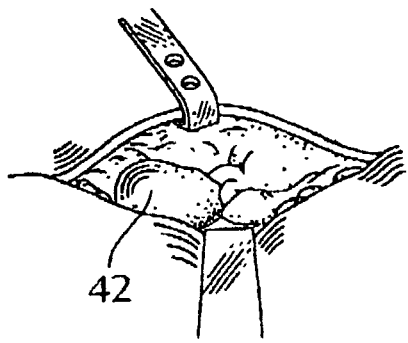
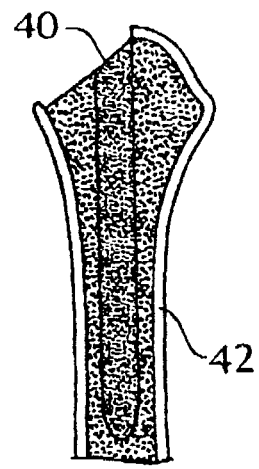
Fig. 23    Fig. 24
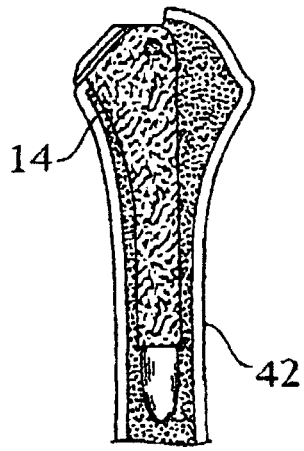
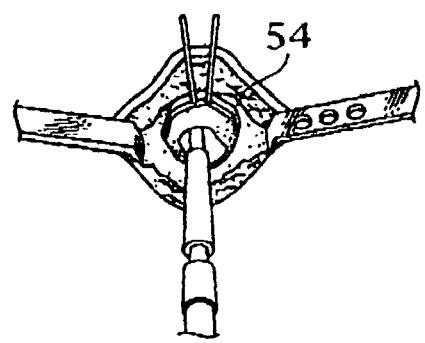
Fig. 25    Fig. 26
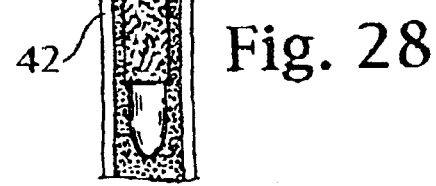
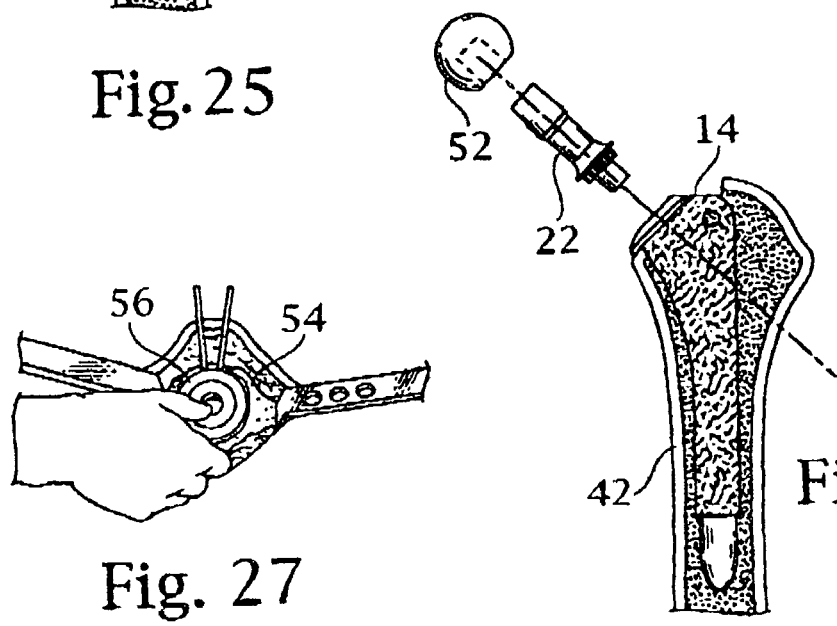
Fig. 27    Fig. 28

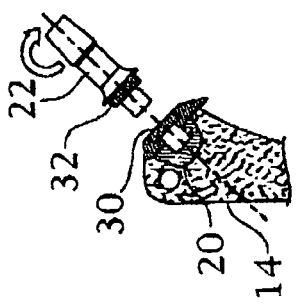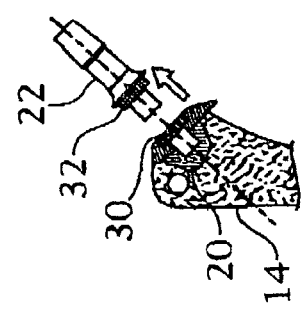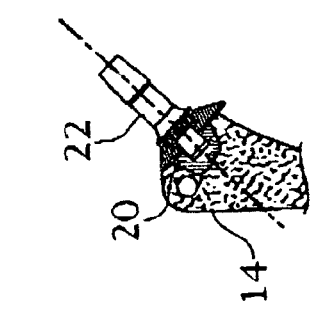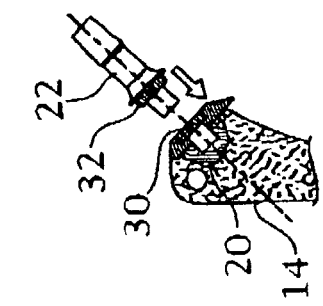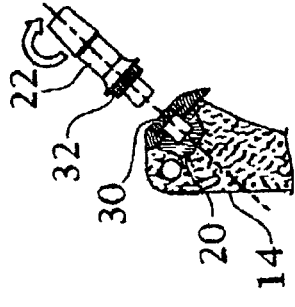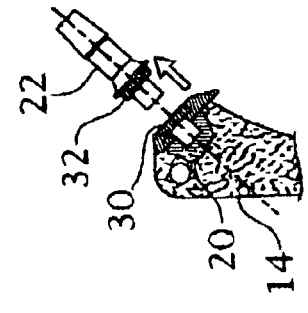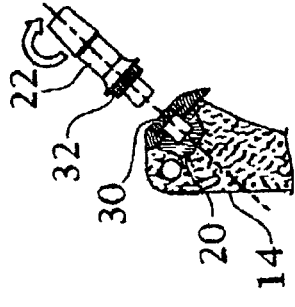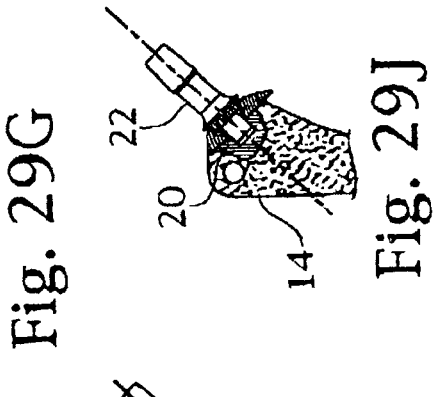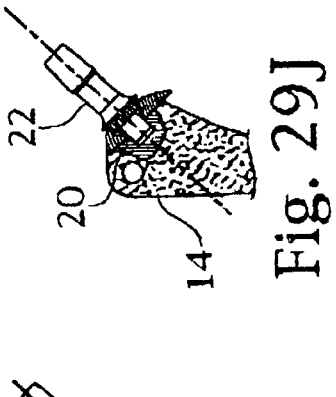

MODULAR NECK FOR FEMUR REPLACEMENT SURGERY

CROSS REFERENCE TO RELATED APPLICATION

The present invention is a continuation-in-part application of application Ser. No. 09/505,876, filed Feb. 17, 2000, now U.S. Pat. No. 6,464,728, which in turn, is a continuation-in-part of application Ser. No. 09/059,698, filed Apr. 14, 1998, now abandoned, the disclosure of which are incorporated in their entirety by reference herein.

BACKGROUND OF THE INVENTION

The present application relates to a prosthesis for femur replacement surgery and more particularly to a prosthesis which receives a modular neck assembly selected for a desired neck length, neck angle, anteversion and offset.

Surgery to replace the femur in total joint surgery involves the insertion of a stem in a cavity formed in the femur. The end of the stem extending from the cavity has a neck which is formed at an angle and the neck is mated with a socket in the hip. Every patient requires individual fitting due to the unique anatomical requirements of the particular patient. A prosthesis in which the stem and neck are a unitary device requires that the surgeon have a large quantity of prostheses available to provide a correct bio-mechanical function of the prosthesis with the patient. It is very costly to maintain a large inventory of prostheses and, despite the number of prostheses available, quite often the appropriate size and angle are not completely met.

More recently, modular prostheses have been designed to overcome this longstanding problem. The modular designs have each focused on a different aspect of the prosthesis. U.S. Pat. No. 4,919,670 to Dole et al disclose a tapered cylindrical lock mechanism disposed on the proximal end surface of the stem and the head mechanism including a complementary tapered aperture for receiving the cylindrical lock mechanism in a rigid mechanical coupling engagement. In U.S. Pat. No. 4,995,883, Demane et al disclose a modular hip prosthesis which can be custom fitted to a patient before surgery. A plurality of prostheses bodies, pads, heads, collars and extension sleeves are offered in various sizes. An elongated bolt extends through the prosthesis body and is connected to the extension sleeve. Luman, in U.S. Pat. No. 5,002,578 discloses a modular hip stem prosthesis apparatus which includes a hip stem with an integral, enlarged shoulder and a neck section mountable to the hip stem which are releasably interconnected with a bolt. The annular relation between the side arm and the longitudinal axis of the hip stem is selectively predetermined. In U.S. Pat. No. 5,002,581, Paxson et al disclose a modular hip joint prosthesis with adjustable angular variation. This variation is made possible by having the axis of the connection part of the stem and neck being angularly offset from the axis of the body of the stem and neck, respectively. Pappas et al, in U.S. Pat. No. 5,030,234 disclose a modular stem prosthesis which has a stem connected to an extension with a slip fit interconnection. Engagement between the stem and the extension is provided by deflectable end portions of one component of the prosthesis which are engaged in a mating deformation with the other component. Fallin, U.S. Pat. No. 5,108,452, is a continuation-in-part of Demane et al and discloses removable pads attached to the prosthesis body with a wedge to lock the connection between the prosthesis and the hip joint. In U.S. Pat. No. 5,286,260, Bolesky et al disclose a modular hip prosthesis for replacement of a portion of the femur comprising a kit that includes an upper and lower portion. A neck member is also provided to rigidly attach the head member to the body member. McTighe et al in U.S. Pat. No. 5,653,765 discloses a modular hip stem prosthesis having a neck member extending angularly outward from the shoulder peice and configured to receive a spherical hip ball for insertion into the hip socket. A locking screw secure joins the shoulder piece with the stem.

A further complication in the total joint surgery to replace the femur is that clinically, the metal of the prosthesis is not compatible with the bone on a modular scale. The different moduli of the bone and the metal causes a stress path to pass through the more rigid material and the stress between the bone and metal occurs distally shielding the proximal femur from stress. This results in atrophy of the proximal femur and pain to the patient and eventually, possible failure. To alleviate this problem, Averill et al in U.S. Pat. No. 4,888,023, disclosed a prosthesis with a fixation resistant finish on the external peripheral surface of the distal tip. The distal tip is selectively removable and replaceable. In U.S. Pat. No. 4,892,546, Kotz et al disclose an adjustable prosthesis for a joint bone having an elongated inner sleeve and an outer sleeve. The inner sleeve is telescopically slidable within the outer sleeve but is not rotatable. The inner sleeve includes a threaded spindle nut and a threaded spindle which are positioned within the inner sleeve. In U.S. Pat. No. 5,057,101, Dorr et al disclose a femoral prosthesis with a centering sleeve wherein the sleeve is removably attached midway along a stem of the prosthesis. Removable sleeves are disclosed.

Montagne in European Patent No. 0 201 407 A1 discloses a prosthesis with connecting members which are adjustable with an octagonal fitting. A sleeve is not disclosed on the shank of the prosthesis. Frey in European Patent No. 0 187 903 A1 discloses an adjustable hip joint prosthesis with an outer sleeve having an inner polyethylene liner. The outer sleeve has an outer surface with self-tapping threads to be screwed to the femur. In WIPO publication WO 94/07438, Tronzo discloses a bearing mechanism built into a femoral component which has a sleeve. The sleeve is disposed at the distal portion of the stem and buttresses a bearing retaining shoulder. Walker in WIPO publication WO 91/03992 discloses a prosthesis with a plastic sleeve having a non-uniform bore.

Despite the recognition and activity directed to solving these longstanding problems, none of the above-identified patents have been widely accepted and prostheses based on these references have not made a significant impact in the field. The problem still exists.

BRIEF SUMMARY OF THE INVENTION

It is an object of the present invention to provide a prosthesis for use in femur replacement surgery which has a modular neck assembly which is selected to provide a predetermined neck length, neck angle and anteversion to meet the unique anatomical requirements of the individual patient and provide the correct force line to transfer the stresses into the anatomical plane of the femur.

It is a further object of the present invention to provide a dual locking means between the adapter and the main body portion of the prosthesis.

It is yet another object of the present invention to permit the surgeon to provide a prosthesis adapted for the individual patient selected from a series of adapters while maintaining a minimum number of prostheses in stock.

It is still another object of the present invention to provide a prosthesis having a porous coating to facilitate biological in-growth.

In accordance with the teachings of the present invention, there is disclosed a prosthesis for hip replacement surgery which includes a main body portion and further includes a selected one of a series of adapters for accommodating the device to a particular patient. The prosthesis has a tapered bore formed in the main body portion of the device. Each adapter has a shank formed with a taper corresponding to the tapered bore in the main body portion of the device, thereby accommodating tolerance accumulations and providing a first locking means between the adapter and the main body portion of the device. Each adapter further has a first series of circumferentially-spaced teeth formed thereon distally of and adjacent to the tapered shank of the device. The main body portion of the device has a second series of corresponding circumferentially-spaced teeth formed thereon distally of and adjacent to the tapered bore, for circumferential indexing of the adapter with respect to the main body portion of the device for adjustment of the device to a particular patent during hip replacement surgery. The first and second series of teeth are formed with complementary tapers, respectively, thereby providing a second locking means between the adapter and the main body portion of the device.

In further accordance with the teachings of the present invention, there is disclosed a prosthesis for femur replacement surgery having an orthopedic prosthesis, wherein a first member cooperates with a selected one of a plurality of second members, and wherein said selected one of the second members is circumferentially adjusted with respect to the first member for optimum application to a specific patient. A first set of internally-tapered teeth on the first member cooperating with a corresponding second set of externally tapered teeth on said selected one of the plurality of second members. The corresponding first and second sets of teeth have cooperating respective tapered surfaces. The corresponding first and second sets of teeth with their cooperating respective tapered surface have respective dimensions and tolerances to assure that the respective tapered surfaces are engaged and locked together before the corresponding first and second sets of teeth bottom and respect to each other.

A method of using the prosthesis is disclosed.

These and other objects of the present invention will become apparent from a reading of the following specification taken in conjunction with the enclosed drawings.

BRIEF DESCRIPTION OF THE DRAWINGS

FIG. 1 is a side elevation view of the assembled prosthesis of the present invention.

FIG. 2 is a back elevation view of FIG. 1.

FIG. 3 is a front elevation view of FIG. 1.

FIG. 14 is a side elevation view of the modular neck assembly having a spherical head formed on the second end portion.

FIG. 15 is a side elevation view of the prosthesis of the present invention which does not have a sleeve.

FIG. 23 is a perspective view showing the incision in the hip of the patient.

FIG. 24 is a cross-section view showing reaming of the femur of the patient forming a canal therein.

FIG. 25 is a cross-section view showing insertion of the stem of the main body of the prosthesis into the canal in the femur.

FIG. 26 is a perspective view showing reaming of the acetabulum.

FIG. 27 is a perspective view showing trial insertion of a liner into the reamed acetabulum.

FIG. 28 is a perspective, partial cut away view showing trialing of the adapter in the main body.

FIGS. 29A–29J is a series of perspective, partial cut away views showing trial installation of an adapter.

DESCRIPTION

Figure 4:
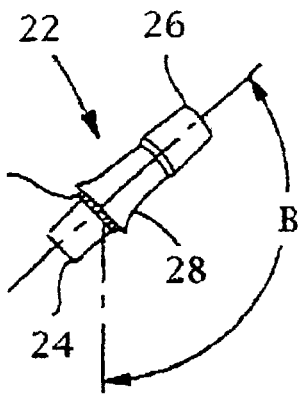
FIG. 4 is a side elevation view of a modular neck assembly showing an angle with respect to the stem.

Referring now to FIGS. 1–3, the prosthesis 10 of the present invention used in femur replacement surgery has a main body portion (stem) 12 which has an enlarged upper portion 14 and an opposite lower portion 16. The lower portion 16 preferably is tapered to a point. A sliding sleeve 18 may be received on the lower portion 16 as will be described.

A blind tapered bore 20 is formed in the enlarged upper portion 14 of the stem 12. The center line of the blind bore 20 is formed at an angle with respect to the vertical axis of the stem 12. Means are formed in the bore or around the bore 20 in the surface of the upper portion 14 to rotationally engage and lock an adapter (modular neck assembly) 22 at a selected degree of rotation within the bore 20 and to prevent any further rotation. The stem 12 may be available in a variety of sizes which have different lengths and which further is designated as small medial aspect, being more narrow in the upper portion 14.

Figure 5:
FIG. 5 is a bottom end view of the modular neck assembly.
Figure 6:
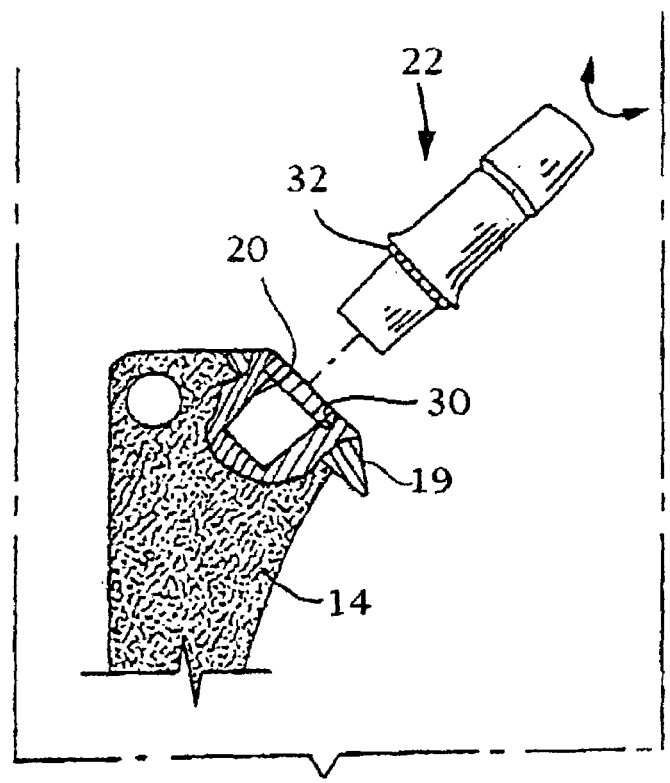
FIG. 6 is an enlarged partially cut away side elevation view of the bore formed in the upper portion of the stem of the prosthesis and the modular neck assembly to be received therein.

A modular neck assembly 22 (FIGS. 4–5) has a first end portion (shank) 24 and an opposite second end portion 26. The length of the second end portion 26 preferably, is greater than the length of the first end portion 24 and may be formed to a desired length. Preferably a flared shoulder 28 is formed between the first end portion 24 and the second end portion 26. The first end portion 24 is formed with a Morse type taper and the bore 20 in stem 12 has a corresponding Morse type taper such that when the modular neck assembly 22 is joined to the stem 12, the modular neck assembly 22 is securely retained therein. Preferably, the taper $t_1$ in both the shank 24 and the bore 20 is approximately 3° with respect to a center line through the shank 24 received in the bore 20 (FIG. 6).

Figure 8:
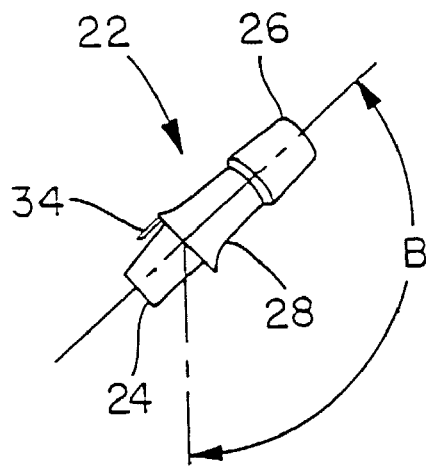
FIG. 8 is a side elevation view of another embodiment of a modular neck assembly showing an angle with respect to the stem.
Figure 9:
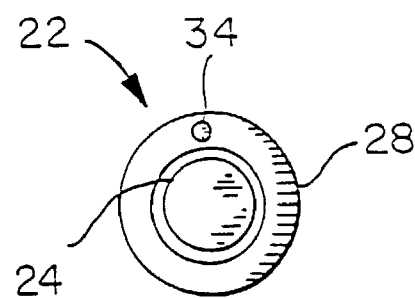
FIG. 9 is an end view of the embodiment of FIG. 8.
Figure 10:
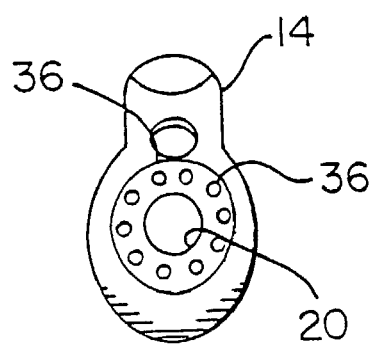
FIG. 10 is an enlarged top elevation view showing the surface and bore of the stem to receive the modular neck assembly of FIG. 8.
Figure 11:
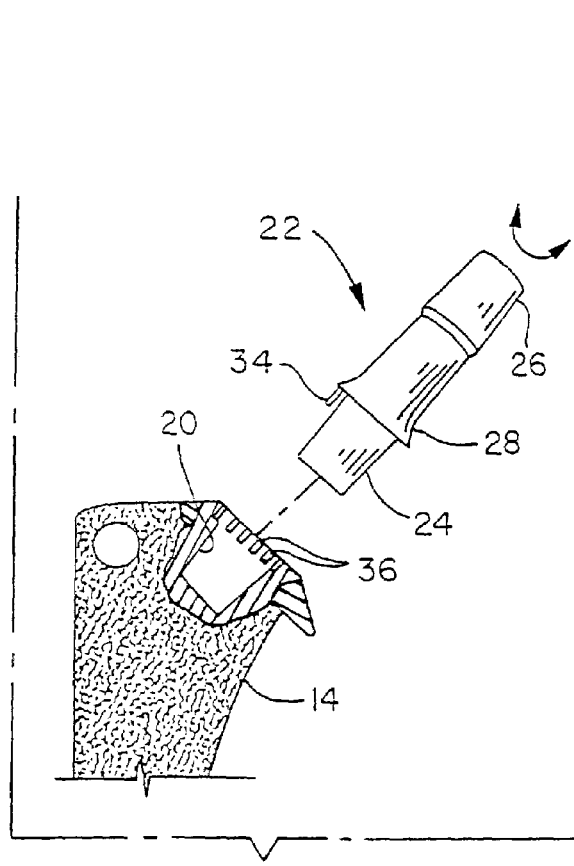
FIG. 11 is an enlarged, partially cut-away, side elevation view showing the embodiment of FIG. 8 received in the bore in the stem.
Figure 12:
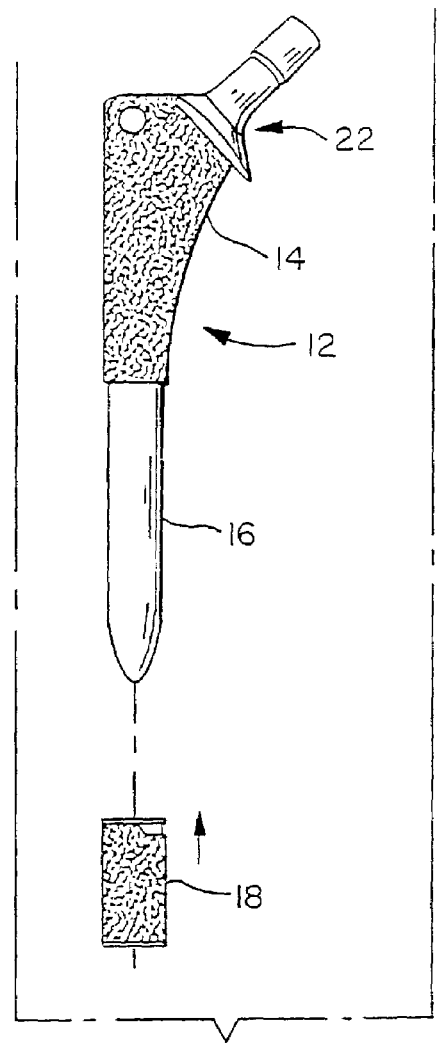
FIG. 12 is a view of FIG. 1 with the sleeve removed.
Figure 13:
FIG. 13 is a cross-sectional view taken across the lines 13—13 of FIG. 1.

In order to provide the surgeon with a modular neck assembly 22 which most nearly corresponds with the anatomy of the patient with respect to the angle between the femur and the hip socket (i.e., customized), a series of modular neck assemblies 22 of the present invention are formed. Each adapter of the series has an angle between the first end portion 24 and the second end portion 26 of the modular neck assembly 22. The angle between the first portion 24 and the second portion 26 is different in each adapter 22 of the series, hence the selected angle with respect to the vertical axis of the stem 12 is different for each adapter of the series. FIGS. 4 and 8 show the angle B ranging from 110° to 140°, although other angles could be provided.

Figure 7:
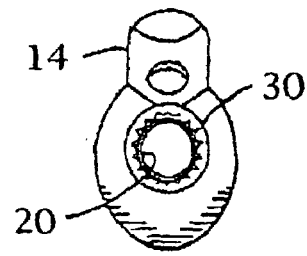
FIG. 7 is an elevation view showing the surface and bore in FIG. 6 to receive the modular neck assembly having indices thereon.

The surgeon is given additional flexibility of configuring the present invention with respect to the anatomical requirements of the patient. The anteversion of the modular neck assembly 22 with respect to the stem 12 is adjustable to a selected angle as required by the individual patient. Anteversion is the angle at which the neck assembly protrudes from the proximal end of the femur. As noted above, means for rotational engagement are formed in or around the bore 20 to engage the modular neck assembly 22 at a selected degree of rotation when the modular neck assembly 22 is disposed in the bore 20. FIGS. 5–7 show one embodiment of the means. In order to reproducibly quantify the rotational engagement, a plurality of indices 48 are provided circumferentially around the bore 20 in the upper portion 14 of the main body 12. The indices 48 may be arbitrary numbers or may be actual angular indicators. An index 50 is formed on the adapter 22 to be aligned with the selected index 48 adjacent to the bore 20. In this manner, the surgeon may trial the disposition of the adapter with respect to the main body 12 during the procedure as will be described. A plurality of spaced-apart teeth 30 or similar keying means are formed circumferentially within the bore 20. A complementary plurality of cooperating spaced-apart teeth 32 (or keying means) are formed about the first end portion of the modular neck assembly 22 near the flared shoulder 28. The degree of rotation of the modular neck assembly 22 with respect to the center line of the bore 20 can be selected by the surgeon. This produces the anteversion desired (angle A in FIG. 2). The anteversion can be to the right or to the left of the vertical axis of the stem 12 depending upon the rotation of the modular neck assembly 22 and as shown by the curved arrow in FIG. 6. Both the series of teeth 30 in the bore 20 and the series of teeth 32 on the adapter are tapered as will be described.

Also, when the modular neck assembly 22 is rotated with respect to the bore 20, the modular neck assembly 22 becomes offset with respect to the vertical axis of the stem 12. The offset is the angle formed between the second end portion 26 of the neck assembly and a vertical plane drawn through the bore 20.

Another embodiment of the means for rotational engagement between the bore 20 and the modular neck assembly 22 is shown in FIGS. 8–11. In this embodiment, a peg 34 is formed along a center line of the modular neck assembly 22 and approximately parallel to the first end portion of the modular neck assembly 24. Preferably, the peg 34 depends from the flared shoulder 28. A plurality of spaced-apart peg holes 36 are formed in upper portion 14 of the stem 12. The peg holes 36 are formed radially of the bore 20. Preferably, the peg holes 36 are formed on the surface of the upper portion of the stem but could be within the base of the bore 20 with the peg 34 being formed extending from first end portion 24 of the modular neck assembly. The modular neck assembly 22 is inserted into the bore 20 with the peg 34 being received in a selected peg hole 36 to provide the desired degree of anteversion (right or left).

A further advantage of either embodiment of the means for rotational engagement is that further rotation of the modular neck assembly 22 within the bore 20 is prevented during or after the surgical procedure. In this manner, the surgeon is assured that the prosthesis is customized for the individual patient and is locked in place.

The second end portion 26 of the modular neck assembly 22 has a Morse type taper formed thereon to engage a Morse type taper in a socket in a femoral head 52 which is placed within the hip of the patient. However, if desired, the second end portion 26 of the modular neck assembly 22 may have formed thereon a spherical head 38. This embodiment may reduce the costs of inventory by avoiding the need to stock additional sockets (FIG. 14).

Figure 16:
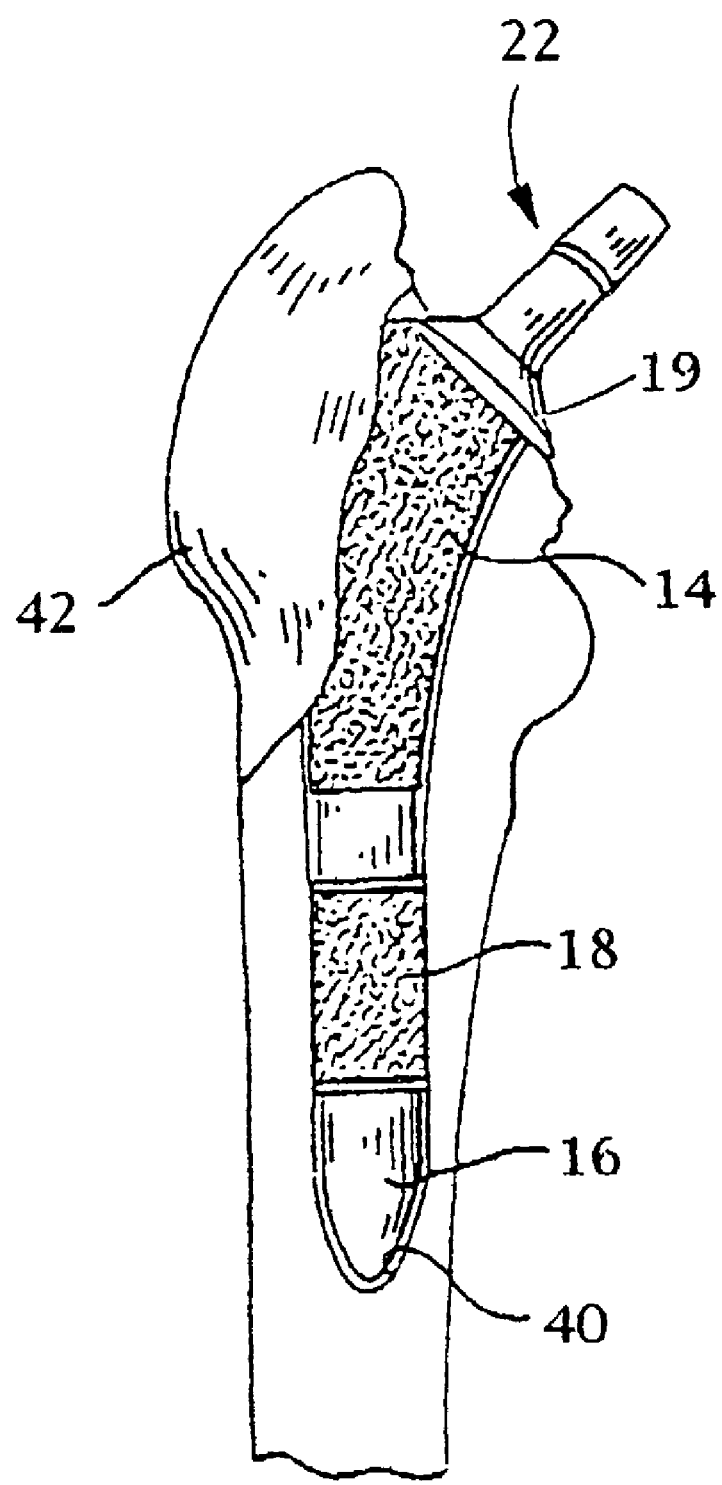
FIG. 16 is a partial cut-away view of the femur having the prosthesis with a sleeve received in the canal in the femur.

The distal end of the stem 12 is tapered to a point which assists the surgeon in directing the prosthesis into the canal formed in the femur. The prosthesis 10 of the present invention may have a lower portion 16 of the stem 12 which has a sleeve 18 received thereon. The sleeve 18 preferably surrounds the circumference near the tip of the lower portion 16 of the stem 12 (FIGS. 1, 2, 12 and 13). The sleeve 18 is unitary which means that the inner circumference of the sleeve is directly opposed to the lower portion of the stem 12 with no intervening members such as a inner sleeve or tube as disclosed in the prior art. Preferably, the sleeve 18 is press-fit into a canal 40 formed in the femur by the surgeon. The canal 40 is formed having a diameter slightly less than the outer diameter of the sleeve 18 at a distance from the top of the canal in the femur which is predetermined by the surgeon. The sleeve 18, when so press-fitted, has a uniform inner diameter which receives the outer diameter of the lower portion 16 of the stem 12 (FIG. 16). An intermediate annular shoulder 44 is formed on the stem 12 at the interface between the upper portion 14 and the lower portion 16. The lower portion 16 of the stem 12 has a uniform diameter above the tapered point to the annular shoulder 44 and is highly polished. The axial length of the sleeve 18 is substantially less than the axial length of the lower portion 16 of the stem 12 between the shoulder 44 and the tip of the stem. Thus, when the surgeon inserts the stem 12 of the prosthesis 10 into the canal in the femur, the lower portion of the stem 12 is received in the sleeve 18. When the patient moves his/her leg after surgery, the stem 12 may move circumferentially with respect to the implanted sleeve 18 and may also have micro-motion along the vertical axis of the stem 12 with respect to the implanted sleeve 18. The sleeve 18 does not abut the annular shoulder 44. Thus, the implanted prosthesis still has motion with respect to the femur so that the stress between the bone and the metal prosthesis is distributed across the entire length of the prosthesis and the proximal femur is not shielded from stress. In this manner, atrophy in the proximal femur is significantly reduced.

It is preferred that a porous coating be applied to the outer surface of the upper portion of the stem 12 and the sleeve 18. The porous coating is formed from metal beads in the range of −40/+65 to −25/+35 mesh size. The beads are formed from the same metal as the prosthesis and are preferred to be cobalt-chrome-molybdenum. The beads are retained onto the outer surface of the prosthesis by a suitable binder and subjected to a sintering process at approximately 2,400° F. in a vacuum furnace. The porous coating is hot isostatic pressed at approximately 15,000 psi at approximately 2,225° F. This porous coating facilitates the biological in-growth and on-growth of cancellous bone to improve the skeletal attachment of an implanted device such as the prosthesis used in orthopedic surgery. The addition of hydroxyapatite to the surface of the spherical beads enhances biological in-growth. The biological in-growth effects an anchoring of the prosthesis to the femur.

To increase torsional stability between the implant, bone cement and the femur, a variety of surface finishes are applied to a prosthesis like the R120™ Femoral stem offered by OTI, Inc. The distal portion of the stem may have a polished finish between the ranges of 2–15 RA (micro inches). The proximal portion may have a rougher finish between the ranges of 15–30 RA. The "teardrop cavity" on Anterior and Posterior sides may have a rougher satin finish of 30–80 RA. The finish roughness in areas noted above may be increased or decreased for a respective femoral stem design. The entire stem surface may have a polished surface of 1–15 RA for specific applications. The modular stem may also be used in conjunction with polymethylmethacrylate (PMMA-bone cement) for fixation in the femur if the bone stock is not suitable for biological in-growth. In that case, a porous surface is not utilized.

It is not essential that the prosthesis have a sleeve on the distal end of the stem. If desired by the surgeon, the stem may be cemented into the canal 40 in the patient's femur.

FIG. 15 shows a prosthesis 10 without a sleeve and having a porous coated surface extending onto the lower portion of the stem.

As shown in FIGS. 17–20, the series of teeth 30 in the bore 20 and the series of teeth 32 on the adapter 22 are tapered. The taper $t_2$ is an angle of approximately 5° with respect to a center line through the tapered bore 20 in the main body portion 12 and through the shank of the adapter 22 when the shank is received in the bore. The series of teeth 30, 32 engage one another. The teeth 32 on the adapter 22 are external and are tapered. The teeth 30 in the bore 20 are internal and are tapered. Together with the fitting between the tapered bore 20 and the tapered shank 24, the tapered engaging teeth 30, 32 form a double lock between the main body and the adapters. Thus, when the prosthesis is implanted in the patient at a position which most nearly cooperates with the anatomy of the patient, there is assurance that there will be no subsequent movement of the prosthesis and no failure of the surgery due to such movement.

Figure 17:
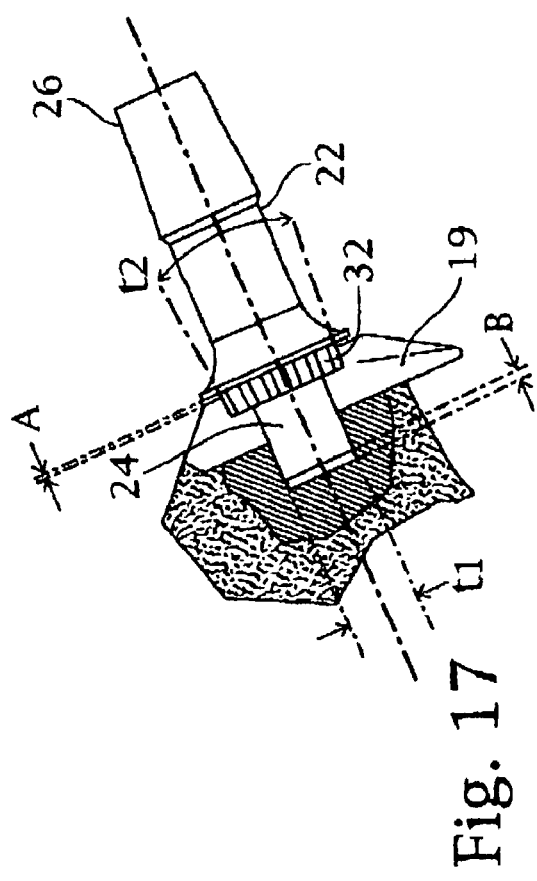
FIG. 17 is a partial cut away view of the tapered shank of the modular neck assembly received in the tapered bore in the main body of the prosthesis showing a minimum clearance.

A further benefit of the cooperating tapered teeth 30, 32 is that tolerance accumulations which occur in production are accommodated. FIG. 17 illustrates the cooperation between the tapered teeth and the relative disposition of the adapter 22 with respect to the main body of the stem 12 when the cumulative tolerances of all the components are minimum.

Figure 18:
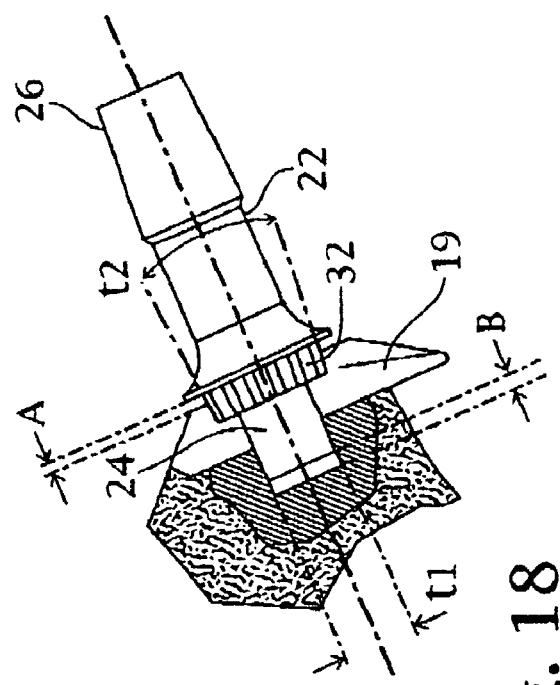
FIG. 18 is the same as FIG. 17 showing maximum clearance.
Figure 19:
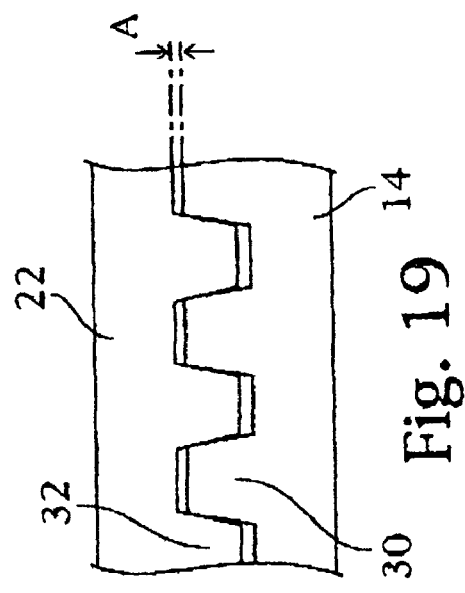
FIG. 19 is an enlarged view of a portion of the teeth of FIG. 17.
Figure 20:
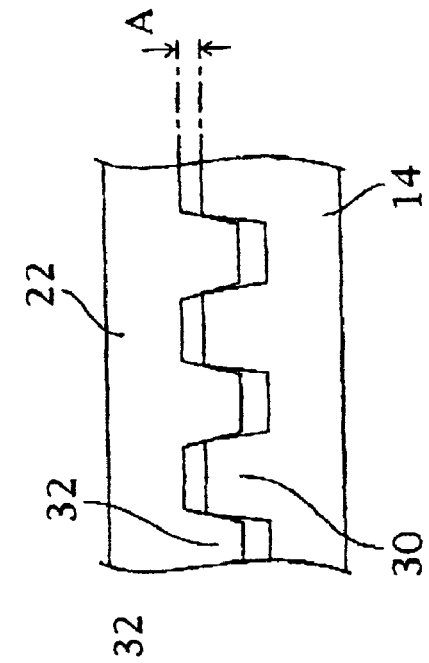
FIG. 20 is an enlarged view of a portion of the teeth of FIG. 18.

The clearance between the sets of teeth is shown as A. The clearance between the first end portion 24 of the modular neck assembly 22 and the base of the bore 20 in the stem 14 is shown as B. FIG. 18 illustrates the same when the cumulative tolerances are maximum. The corresponding clearances are shown as A' and B'. Under both minimum and maximum conditions, the tapered surface on the teeth 34 in the bore and the tapered surface on the teeth 32 on the adapter engage and lock together before the sets of teeth bottom with respect to one another (FIGS. 19–20).

Figures 21, 22:
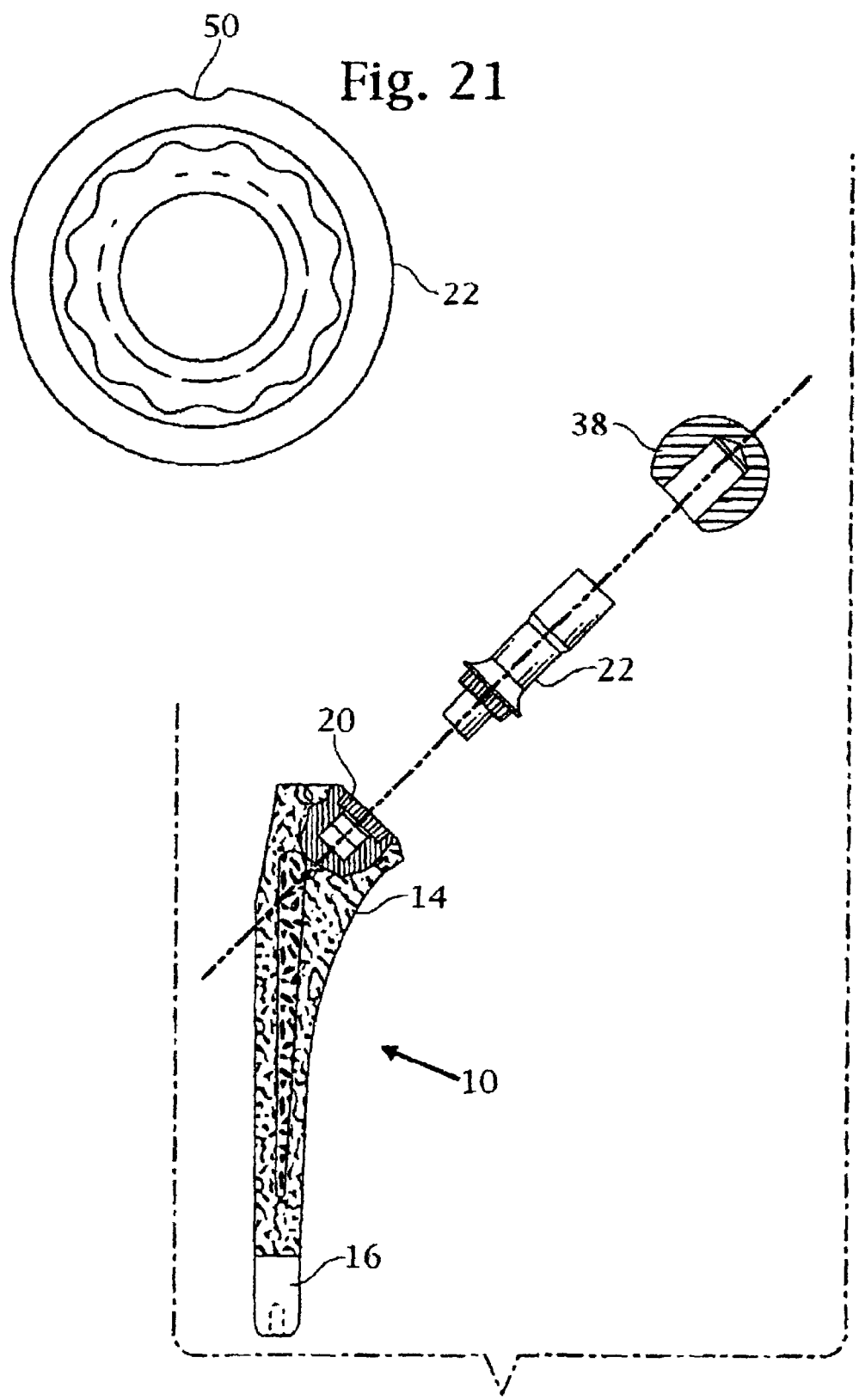
FIG. 21 is an end view of an adapter showing the index thereon.
FIG. 22 is partially cutaway side view of the prosthesis without a shoulder and the modular neck assembly and spherical head.

As shown in FIGS. 1–3, 6, 16, 17 and 18, a collar 19 is formed on the upper portion 14 of the main body portion 12. The collar 19 is around the tapered bore 20 and extends outwardly from the upper portion of the main body portion 12. The collar 19 abuts, and is supported on the femur. Alternately, as shown in FIG. 22, the upper portion 14 may be formed without the collar. The top surface of the prosthesis is formed at an angle with respect to the upper portion 14 and the tapered bore 20 is formed in the top surface. This collarless embodiment may be used for the minimal invasive surgical approach. It decreases the surgical procedure time and accelerates wound healing and patient recovery. The modular stem of the present invention is ideally suited for small aperture surgery and can be installed in the patient with accuracy due to the modularity of components in situ. A greater certainty of outcome is obtained because the prosthesis more closely resembles the correct anatomy and biomechanical force lines.

Figure 30:
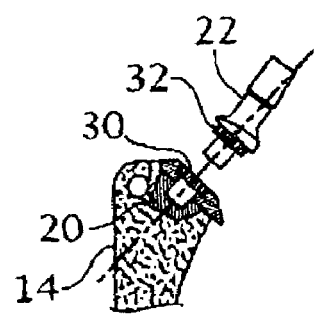
FIG. 30 is a perspective view showing trialing of a neck assembly having a different angle.
Figure 31:
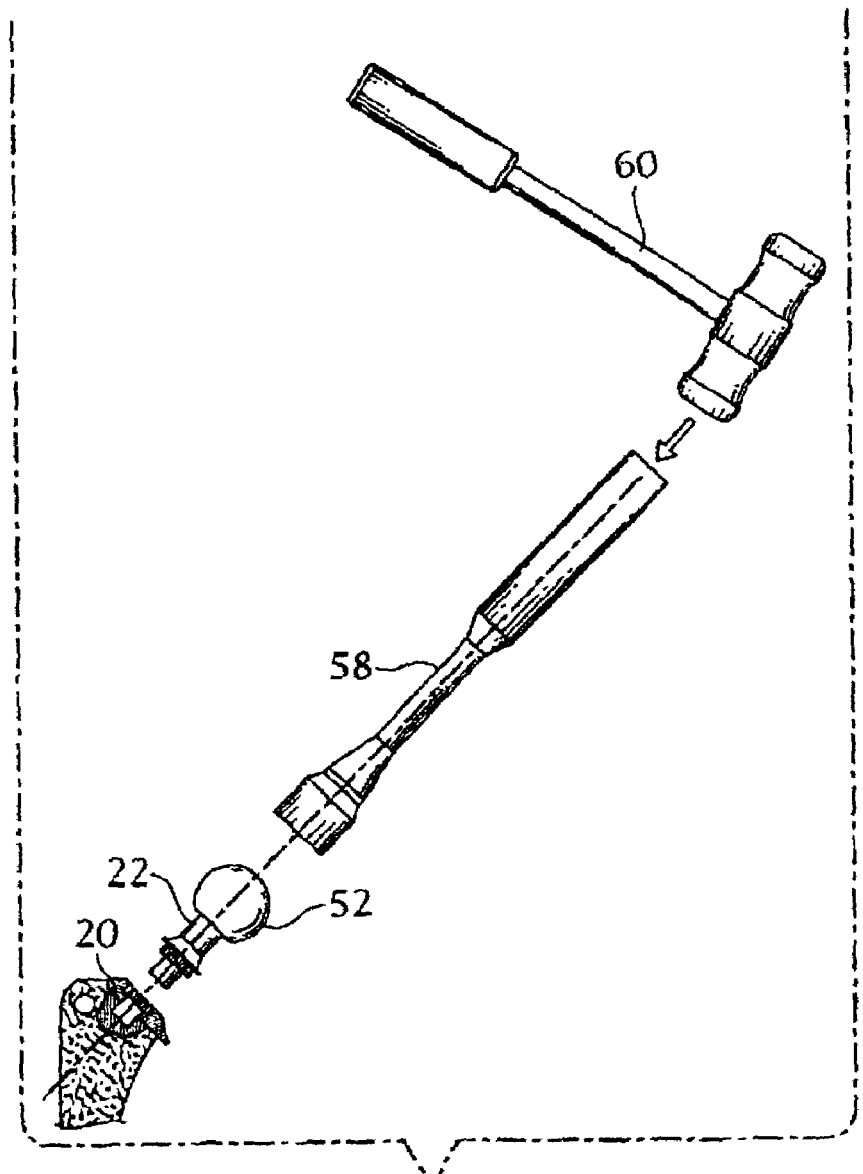
FIG. 31 is a perspective view showing final installation of the modular femur head and the adapter into the main body of the prosthesis.

In use, the surgeon carefully measures the angle between the patient's femur and hip socket and the degree of anteversion of the patient's femur. Also, the length of the patient's legs are carefully measured. Based on these measurements the surgeon meticulously calculates the type of prosthesis required for the particular patient. As shown in FIGS. 23–28 the surgeon incises the hip to expose the femur 42 and reams the femur to form a canal 40 in the patient's femur, the canal 40 having a predetermined diameter. If desired, a sleeve 18 is press fitted into the canal in the femur at a predetermined distance from the top of the canal 40. The stem of the main body is inserted in the canal 40. The acetabulum of the patient is reamed and an acetabulum trial cup sizer 56 is placed in the reamed acetabulum. A trial liner is placed in the acetabulum trial cup sizer. A modular neck assembly 22 is selected from the series which is calculated to have an angle between the second end portion 26 and the vertical axis of the stem 12 which most closely correspond with the angle between the patient's hip socket and the femur. The modular neck assembly 22 is rotated with respect to the bore 20 in the stem 12 which most closely corresponds with the degree of anteversion of the patient's femur (FIGS. 29A–29J). The indices 48 in the main body 12 and the index 50 on the adapter 22 (FIG. 21) are used to reproduce the desired rotation. The modular neck assembly 22 is inserted into the bore 20 to trial the modular neck assembly 22 to the stem 12 as the predetermined angle and degree of anteversion. Other modular neck assemblies having different angles are progressively selected from the series of adapters 22 and are trialed by the surgeon to assure the selection of the modular neck assembly which most closely matches the anatomy of the patient (FIG. 30). After selection of the preferred modular neck assembly 22, the trial liner and acetabulum trail cup sizer 56 are removed. The femoral head 52 is connected to the selected modular neck assembly 22. As shown in FIG. 31, the selected modular neck assembly is driven into the bore 20 using a femoral head compactor instrument 58 and a surgical mallet 60 such that the series of tapered teeth 32 in the modular neck assembly engage and lock with the series of teeth 30 in the bore. The prosthesis 10 is connected to the hip socket.

Preferably, the entire prosthesis, including the stem 12, the modular neck assembly 22 and the sleeve 18 are formed substantially from metal. A preferred metal is a cobalt-chrome-molybdenum alloy which is very compatible with the tissue and bones of human beings. The prosthesis is not limited to this metal but may be made of other metals including titanium.

Thus, this present invention provides a prosthesis which more closely reproduces the anatomy of the individual patient. It enables the surgeon to maintain a smaller inventory of components as a kit or series of adapters from which to choose while providing a greater versatility in sizes. This results in a cost reduction. The components of the prosthesis are amenable to mass production which further reduces unit costs. Furthermore, the prosthesis with the sleeve avoids stress and atrophy in the femur after implantation.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. In a hip prosthesis including a modular neck adapter having a tapered shank on one end thereof along a first axis and further including a main body portion having a face provided with a tapered bore having an opening to receive the tapered shank on the modular neck adapter, and wherein the tapered shank and the tapered bore are devoid of teeth or splines, the improvement which comprises a counterbore formed in the face of the main body portion, the counterbore being disposed adjacent and circumferentially to the tapered bore and opening on the face of the main body portion, a shoulder on the modular neck adapter, the shoulder being provided with tapered indexing locking teeth cooperating with correspondingly tapered indexing locking teeth on the counterbore in the main body portion, wherein the prosthesis may be readily adapted by the orthopedic surgeon to the bodily configuration of the specific patient in the operating room; and wherein, when thus installed in the patient, the end of the tapered shank on the modular neck adapter does not bottom within the tapered bore in the main body portion, and the shoulder on the modular neck adapter does not engage the face of the main body portion.

2. The improvement of claim 1, wherein the corresponding taper between the complementary indexing locking teeth is greater than the corresponding taper between the tapered shank on the modular neck adapter and the tapered bore in the main body portion, respectively, thereby providing a superior locking engagement therebetween.

3. The improvement of claim 2, wherein the tapered shank on the modular neck adapter and the tapered bore in the main body portion are both tapered at an angle of approximately 3° with respect to a center line through the respective tapered shank and the tapered bore.

4. The improvement of claim 2, wherein the tapered locking teeth on the modular neck adapter and the tapered teeth on the tapered bore are tapered at an angle of approximately 5° with respect to a center line through the respective modular neck adapter and the tapered bore.

5. The improvement of claim 1, wherein the main body portion has a longitudinal axis, and wherein the face of the main body portion is chamfered at an angle with respect to the longitudinal axis of the main body portion.

6. The improvement of claim 1, wherein the modular neck adapter has an opposite end provided with a taper, the opposite tapered end having an axis which is angularly disposed with respect to the first axis of the one tapered shank.

7. The improvement of claim 1, wherein the teeth are radiused having no sharp edges.

8. In a hip prosthesis including a modular neck adapter having a tapered shank on one end thereof along a first axis and further including a main body portion having a face provided with a tapered bore having an opening to receive the tapered shank on the modular neck adapter, the improvement which comprises a counterbore formed in the face of the main body portion, the counterbore being disposed adjacent and circumferentially to the tapered bore and opening on the face of the main body portion, a shoulder on the modular neck adapter, the shoulder being provided with tapered indexing locking teeth cooperating with correspondingly tapered indexing locking teeth on the counterbore in the main body portion, wherein the corresponding taper between the complementary indexing locking teeth is greater than the corresponding taper between the tapered shank on the modular neck adapter and the tapered bore in the main body portion, respectively, thereby providing a superior locking engagement therebetween; wherein the prosthesis may be readily adapted by the orthopedic surgeon to the bodily configuration of the specific patient in the operating room; and wherein, when thus installed in the patient, the end of the tapered shank on the modular neck adapter does not bottom within the tapered bore in the main body portion, and the shoulder on the modular neck adapter does not engage the face of the main body portion.

9. The improvement of claim 8, wherein the tapered shank and the tapered bore are devoid of teeth or splines.

10. The improvement of claim 8, wherein the tapered shank on the modular neck adapter and the tapered bore in the main body portion are both tapered at an angle of approximately 3° with respect to a center line through the respective tapered shank and the tapered bore.

11. The improvement of claim 8, wherein the tapered locking teeth on the modular neck adapter and the tapered teeth on the tapered bore are tapered at an angle of approximately 5° with respect to a center line through the respective modular neck adapter and the tapered bore.

12. The improvement of claim 8, wherein the modular neck adapter has an opposite end provided with a taper, the opposite tapered end having an axis which is angularly disposed with respect to the first axis of the one tapered shank.

* * * * *